(12) United States Patent
Chapman et al.

(10) Patent No.: US 6,773,704 B1
(45) Date of Patent: Aug. 10, 2004

(54) METHODS OF TREATING VASCULAR DISEASE ASSOCIATED WITH CYSTATIN C DEFICIENCY

(75) Inventors: Harold A. Chapman, San Francisco, CA (US); Guo-Ping Shi, San Francisco, CA (US); Peter Libby, Boston, MA (US); Galina K. Sukhova, Swampscott, MA (US); Daniel I. Simon, Waban, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/697,613

(22) Filed: Oct. 26, 2000

Related U.S. Application Data
(60) Provisional application No. 60/162,313, filed on Oct. 28, 1999, now abandoned.

(51) Int. Cl.[7] .......................... A61K 38/16; A61K 38/02; A61K 38/46; C07K 14/00
(52) U.S. Cl. .................. 424/94.1; 424/94.6; 424/94.65; 530/330
(58) Field of Search .............................. 424/94.1, 94.6, 424/94.65; 530/330

(56) References Cited

U.S. PATENT DOCUMENTS

| | | | |
|---|---|---|---|
| 5,157,019 A | 10/1992 | Glover et al. |
| 5,164,295 A | 11/1992 | Kisilevsky et al. |
| 5,262,319 A | * 11/1993 | Iwata et al. |
| 5,270,165 A | 12/1993 | Van Nostrand et al. |
| 5,432,264 A | 7/1995 | Grubb et al. |
| 5,866,318 A | 2/1999 | Rydel et al. |
| 6,033,893 A | 3/2000 | Bandman et al. |
| 6,420,364 B1 | * 7/2002 | Emmanuel et al. |

FOREIGN PATENT DOCUMENTS

WO    WO 94/01139    1/1994

OTHER PUBLICATIONS

Abrahamson et al., 82 Hum. Genet. 223–26 (1989).
Allaire et al., 102 J. Clin. Invest. 1413–20 (1998).
Barrett et al., 120 Biochem. Biophys. Res. Commun. 631–36 (1984).
Bossard et al., 271 J. Biol. Chem. 12517–524 (1996).
Bromme et al., 271 J. Biol. Chem. 2126–32 (1996).
Brown et al., 68 Methods in Enzymology 109–151 (1979).
Buisson et al., 12 FASEB J. 1683–91 (1998).
Calkins et al., 376 Biol. Chem. Hoppe Seyler 71–80 (1995).
Cao et al., 36 Invest. Orphthalmol. Vis. Sci. 1411–19 (1995).
Chapman et al., 141 Am. Rev. Respir. Dis. 698–705 (1990).
Chapman et al., 74 J. Clin. Invest. 1693–700 (1984).
Chowdhury et al., 254 Science 1802–805 (1991).
DeClerck et al., Adv. Exp. Med. Biol. 425:89–97 (1997).
Fabunmi et al., 83 Cir. Res. 270–78 (1998).
Fruebis et. al., *94 J. Clin. Invest.* 392–98 (1994).
Gacko et al., 50(2) Pol. J. Pathol. 83–86 (1999).
Galis et al., 748 Ann. N.Y. Acad. Sci. 501–7 (1995).
Gelb et al., 273 Science 1236–38 (1996).
Gething & Sambrook, 293 Nature 620–625 (1981).
Ghorpade et al., 800 Ann. N.Y. Acad. Sci. 138–50 (1996).

Grainger et al., 1 Nature Med. 74–79 (1995).
Hansson et al., 135 Am. J. Path. 169–75 (1989).
Hirai et al., 30(6) Hum. Pathol. 680–86 (1999).
Hiltke et al., 78(8) J. Dent. Res. 1401–409 (1999).
International Search Report, issued Feb. 15, 2001.
Ishibashi et al., 93 J. Clin. Invest. 1885–893 (1994).
Ishiguro et al., 8 Hybridoma 303–13 (1989).
Johnatty et al., 158 J. Immunol. 2327–333 (1997).
Kafienah et al., 331 Biochem J. 727–32 (1998).
Knox et al., 95 Circulation 205–12 (1997).
Kyse–Andersen et al., 40 Clin. Chem. 1921–26 (1994).
Libby et al., 7 Curr. Opin. Lipidol. 330–35 (1996).
Littlewood–Evans et al., 57 Cancer Res. 5386–390 (1997).
Mason et al., 330 (Pt. 2) Biochem J. 833–8 (1998).
Masucci et al., 275 Science 391–394 (1997).
McCaffrey et al., 100 J. Clin. Invest. 2182–88 (1997).
McMillan et al., 15 Arteriocler. Thromb. Vasc. Biol. 1139–44 (1995).
Merz et al., 173 J. Cell Physiol. 423–32 (1997).
Merrifield et al., 85 J. Am. Chem. Soc. 2149–2154 (1963).
Nycander et al., 422(1) FEBS Lett. 61–4.
Olafsson, 55 Scand. J. Clin. Lab. Invest. 597–607 (1995).
Olsson et al., 1432(1) Biochim. Biophys Acta 73–81 (1999).
Pearce et al., 800 Ann. N.Y. Acad. Sci. 175–85 (1996).
Purcell–Huynh et al., 95 J. Clin. Invest. 2246–257 (1995).
Randers et al., Clin. Chem. Lab Med., 37(4):389–95 (1999).
Reedy et al., 92 Proc. Natl. Acad. Sci. 3849–853 (1995).
Rohde et al., 18 Arterioscler. Thromb. Vasc. Biol. 1765–70 (1998).
Rohde et al., 19 Arterioscler. Thromb. Vasc. Biol. 1695–1699 (1999).
Ridker et al., 46 J. Investig. Med. 391–395 (1998).
Schiller et al., 25 Int. J. Pent. Prot. Res. 171 (1985).
Schonbeck et al., 81 Circ. Res. 448–54 (1997).
Shi et al., 357 FEBS Lett. 129–34 (1995).
Shimode et al., 22 Stroke 860–66 (1991).
Skaleric et al., 34 Arch. Oral. Biol. 301–305 (1989).
Snider, 146 Am. Rev. Respir. Dis. 1615–622 (1992).
Stemmer et al, 164 Gene 49–53 (1995).
Su et al., 70 J. Cell. Biochem. 517–27 (1998).
Sukhova et al., 102 J. Clin. Invest. 576–83 (1998).
Szekanecz et al., 42 Agents & Actions 159–62 (1994).
Tangirala et al., 36 J. Lipid Res. 2320–328 (1995).
Tetley, 48 Thorax 560–65 (1993).
Thompson et al., 96 J. Clin. Invest. 318–26 (1995).
van Ree et al., 305 Biochem. J. 905–11 (1995).
Warfel et al., 166 J. Exp. Med. 1912–917 (1987).
Werb et al., 857 Ann. N.Y. Acad. Sci. 110–18 (1998).

* cited by examiner

*Primary Examiner*—Christopher R. Tate
*Assistant Examiner*—Kailash C. Srivastava
(74) *Attorney, Agent, or Firm*—Ivor R. Elrifi; Cynthia A. Kozakiewicz; Mintz Levin

(57) ABSTRACT

The invention provides methods of treating and preventing vascular diseases, by inhibiting cysteine proteases active at sites of vascular injury, particularly cathepsins K and S, by administering cystatin C or TGF-$\beta_1$. Cystatin C is severely reduced in both atherosclerotic and aneurysmal aortic lesions. Also provided is a method of diagnosing a patient at risk of, or with, vascular injury by detecting low levels of circulating cystatin C.

5 Claims, 3 Drawing Sheets

Figure 2

METHODS OF TREATING VASCULAR DISEASE ASSOCIATED WITH CYSTATIN C DEFICIENCY

This application claims benefit of application Ser. No. 60,162,313 filed Oct. 28, 1999.

TECHNICAL FIELD OF THE INVENTION

This invention relates generally to methods of treating vascular diseases.

BACKGROUND OF THE INVENTION

Atherosclerosis and abdominal aortic aneurysm (AAA) are inflammatory diseases that involve extensive extracellular matrix degradation and vascular wall remodeling. Cardiovascular events correlate with the presence of inflammation, and atheroma tend to rupture at sites of matrix remodeling (Davies et al., 94 Circulation 213–22 (1996); Ghorpade et al., 800 Ann. N.Y. Acad. Sci. 138–50 (1996)).

However, the mechanisms of degradation of the arterial extracellular matrix in these various contexts remain unclear. In particular, cysteine proteases have previously received little consideration in this mechanism, even though macrophages and smooth muscle cells with greatly expanded lysosomal compartments figure prominently in the histopathology of atherosclerotic plaques. Several cysteine endoproteases (cathepsin K, cathepsin L, and cathepsin S, have potent elastolytic activity. Although elastolytic and collagenolytic cysteine proteases may participate in vascular wall remodeling, cathepsin K has only been observed in bone, and only one study has demonstrated cathepsin K mRNA and protein expression in human breast carcinoma (Littlewood-Evans et al., 57 Cancer Res. 5386–390 (1997)).

Although cathepsins are thought to generally reside in and function optimally within acidic lysosomes, cathepsins also function extracellularly at or near the cell surface. Monocyte-derived human macrophages become markedly elastolytic during in vitro culture and predominantly use cysteine proteases to degrade extracellular elastin. In the presence of pro-inflammatory cytokines found in atheroma, cultured smooth muscle cells secrete active cathepsin S capable of degrading extracellular elastin (Sukhova et al., 102 J. Clin. Invest. 576–83 (1998)). Changes in the concentration of cathepsins B and C localized to aortic aneurysm have recently been described (Gacko et al., 50(2) Pol. J. Pathol. 83–86 (1999)), as has increased expression of cathepsin B in the advancing edge of colorectal tumors (Hirai et al., 30(6) Hum. Pathol. 680–86 (1999)).

By regulating protease activities, protease inhibitors also play a pivotal role in tissue remodeling (see, Werb et al., 857 Ann. N.Y. Acad. Sci. 110–18 (1998)). The most abundant extracellular inhibitor of cysteine proteases is cystatin C (see, Barrett et al., 120 Biochem. Biophys. Res. Commun. 631–36 (1984)). Cystatin C is expressed in virtually all organs of the body, and is present in high concentration in biological fluids. However, aside from a rare mutation in cystatin C that leads to its precipitation as amyloid in cerebral blood vessels and causes cerebral hemorrhage, no evidence has thus far implicated cystatin C in disease.

While cystatin C preparations have been described for the treatment of viral w disease (U.S. Pat. No. 5,432,264), protection of the nervous system from papain (Hiltke et al., 78(8) J. Dent. Res. 1401–409 (1999)), diagnosis of amyloidosis (U.S. Pat. No. 5,270,165), and identification of therapeutic agents to prevent neuronal cell death (U.S. Pat. No. 5,866,318), the role of cystatin C in vascular disease remains unclear. Until now, it has been unknown whether cystatin C expression actually changes in situ in diseases in which inflammation is prominent, and how changes in cystatin C levels might be effected. Thus, there remains a need in the art for the elucidation of the role cystatin C plays in vascular disease, including atherosclerosis, and for the development of therapeutics to prevent and treat vascular elastic laminae breakdown.

SUMMARY OF THE INVENTION

The invention is directed to methods of preventing and treating vascular diseases, inflammatory disorders, and vascular tumors by inhibiting cysteine proteases. Specifically, the invention is directed to the inhibition of two cysteine proteases active at sites of vascular injury, cathepsin S and cathepsin K, by cystatin C, but also includes inhibition of other elastolytic proteases, such as cathepsin L.

The pathogenesis of atherosclerosis and abdominal aortic aneurysm involves elastic laminae breakdown. Elastolytic cysteine proteases are overexpressed at sites of arterial elastin damage, but whether endogenous local inhibitors counterbalance these proteases has previously been unknown. While the cysteine protease inhibitor cystatin C is normally expressed in vascular wall smooth muscle cells, cystatin C is severely reduced in both atherosclerotic and aneurysmal aortic lesions. Increased abdominal aortic diameter correlates inversely with serum cystatin C levels. In vitro, cytokine-stimulated vascular smooth muscle cells secrete elastolytic cathepsin S and cathepsin K. The elastolytic activity of these enzymes is blocked by as little as 10 ng/ml of recombinant cystatin C or by transforming growth factor-$\beta_1$ (TGF-$\beta_1$)-induced cystatin C secretion.

The invention provides methods of preventing the development of and treating vascular disease in a subject by administering an inhibitor of a cysteine protease. In one aspect the subject has not been diagnosed with a vascular disease. Examples of vascular diseases include athersclerosis or aneurismal aortic lesions. Cysteine proteases include cystatins, e.g. cystatin C polypeptide.

In another aspect the invention provides methods of diagnosing a subject at risk of or with vascular disease. A subject at risk is a subject who for example has a family history of vascular disease or has been diagnosed as having a predisposition to vascular disease (e.g., familial hypercholesterolemia or hereditary angiodema). In addition a subject at risk also may be an individual who demonstrates behavioral or environmental risk factors associated with vascular disease. Such factors include for example, gender, advancing age, cigarette smoking, high blood pressure, diabetes, obesity, lack of physical activity, abnormal blood cholesterol homocysteine levels or decreased serum cystatin C levels as compared to a normal healthy adult value. The more risk factors a person has, the greater the likelihood of developing vascular disease. Several of these risk factors are interrelated. Obesity, lack of exercise, and cigarette smoking can raise blood pressure and adversely influence blood cholesterol levels.

BRIEF DESCRIPTION OF THE DRAWINGS

FIG. 2 is a bar graph showing that smooth muscle cells elastase activity is inhibited by recombinant cystatin C. Interferon-γ stimulated smooth muscle cells were co-cultured in serum-free medium with insoluble elastin in the presence of increasing concentrations of cystatin C as indicated in the panel. After 72 hrs, media were collected and soluble radioactivity measured as an index of elastin degradation.

DETAILED DESCRIPTION OF THE INVENTION

Figure 1:
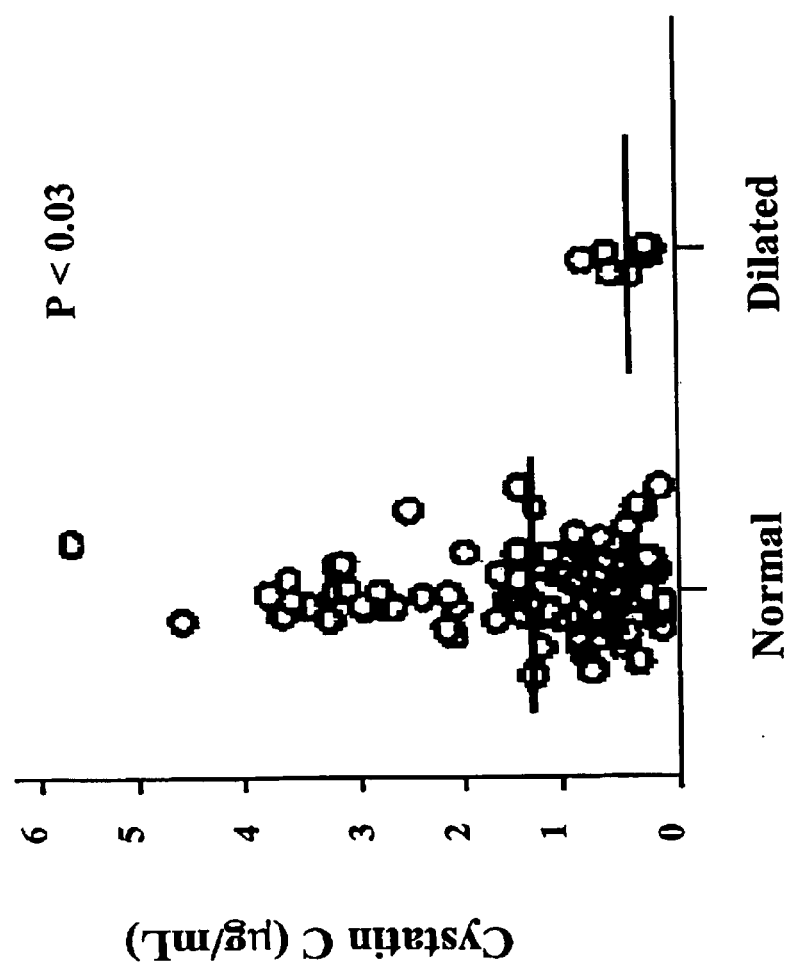
FIG. 1 is a scatter graph illustrating the correlation between aortic diameter and serum cystatin C levels. A cohort of outpatients (n=122) underwent ultrasound measurements of their abdominal aorta and the diameters were correlated with serum cystatin C levels in blood drawn at the time of the outpatient visit. A similar correlation (p<0.04) was observed with indexed aortic diameter (diameter/body surface area) or with aortic diameter as a function of cystatin C corrected for serum creatinine, a known determinant of cystatin C levels.

Introduction Protease inhibitors play a pivotal role in tissue remodeling by regulating protease activity (Werb et al., 857 Ann. N.Y. Acad. Sci. 110–18 (1998)). Among such regulators, the most abundant extracellular inhibitor of cysteine proteases is cystatin C, a 13 kDa protein constitutively secreted shortly after its synthesis (Merz et al., 173 J. Cell Physiol. 423–32 (1997)). Cystatin C belongs to the Type 2 cystatin gene family which cluster, together with other members including cystatins D, S, SA, and SN, on chromosome 2 (Abrahamson et al., 82 Hum. Genet. 223–26 (1989)). Cystatins D, S, and SA are primarily expressed in salivary glands whereas cystatin C is expressed in virtually all organs of the body. Due to its high concentration in biological fluids, cystatin C is probably one of the most important extracellular inhibitors of cysteine proteases.

Despite the prevalence of cystatin C, no evidence had previously elucidated its role in disease, aside from a rare mutation in cystatin C that leads to its precipitation as amyloid in cerebral blood vessels and causes cerebral hemorrhage. It has additionally been shown that, in vitro, alveolar macrophages from cigarette smokers or monocytes stimulated by interferon-γ secrete less cystatin C than unstimulated monocyte/macrophages, raising the possibility of reduced cystatin C levels at sites of alveolar inflammation (Chapman et al., 141 Am. Rev. Respir. Dis. 698–705 (1990); Warfel et al., 166 J. Exp. Med. 1912–917 (1987)). The imbalance of proteolytic and anti-proeteolytic enzyme levels may result in lung destruction (Snider, 146 Am. Rev. Respir. Dis. 1615–622 (1992); Tetley, 48 Thorax 560–65 (1993)), tumor progression (DeClerck et al., Adv. Exp. Med. Biol. 425:89–97 (1997); Calkins et al., 376 Biol. Chem. Hoppe Seyler 71–80 (1995)), and possibly vascular wall remodeling (Allaire et al., 102 J. Clin. Invest. 1413–20 (1998); Fabunmi et al., 83 Cir. Res. 270–78 (1998); Knox et al., 95 Circulation 205–12 (1997); Thompson et al., 96 J. Clin. Invest. 318–26 (1995); McMillan et al., 15 Arteriocler. Thromb. Vasc. Biol. 1139–44 (1995)).

We have discovered that cystatin C is deficient in diseased arteries. As opposed to normal vascular smooth muscle cells, which highly express cystatin C, immunohistochemical analyses of samples from atherosclerotic plaques revealed virtually no cystatin C antigen within plaques. The severe depression of cystatin C antigen levels within smooth muscle cells of atherosclerotic plaques implies a marked change in the functional properties of plaque smooth muscle cells. Normal medial smooth muscle cells express abundant cystatin C. Such changes in the phenotypic properties of these smooth muscle cells are consistent with other evidence that migrating vascular smooth muscle cells have protease and protease inhibitor profiles distinctly different from resident cells of the vessel wall. Smooth muscle cells in atheromatous arteries have augmented matrix metalloproteinase levels (Schonbeck et al., 81 Circ. Res. 448–54 (1997); Galis et al., 748 Ann. N.Y. Acad. Sci. 501–7 (1995)). Macrophages within atherosclerotic and aneurysmal tissues also exhibit increased expression of matrix metalloproteinases (Libby et al., 7 Curr. Opin. Lipidol. 330–35 (1996); Pearce et al., 800 Ann. N.Y. Acad. Sci. 175–85 (1996)).

The marked suppression of cystatin C concurrent with augmented expression of cysteine proteases in atherosclerosis and abdominal aneurysms represents the first acquired cysteine protease inhibitor deficiency in human disease. In contrast to results reported here for cystatin C, tissue inhibitors of matrix metalloproteinases (TIMP) are either unchanged or overexpressed in both atherosclerotic lesions, and abdominal aortic aneurysm. Inflammatory cytokines and growth factors increase the expression of TIMP-1 and TIMP-3 in atherosclerotic lesion-related macrophages and vascular smooth muscle cells (Fabunmi et al., 83 Cir. Res. 270–78 (1998)).

Surprisingly, we have found that TGF-$\beta_1$ is a potent inducer of cystatin C secretion by vascular smooth muscle cells. Low TGF-$\beta_1$ activity explains low levels of lesional cystatin C, and the inverse correlation with aortic dilatation, indicating an additional mechanism by which TGF-$\beta_1$ deficiency contributes to the pathobiology of vascular wall remodeling and atherogenesis. Since IFN-γ-stimulated smooth muscle cells secrete elastolytic cathepsin S, and IFN-γ is present within diseased arteries (Hansson et al., 135 Am. J. Path. 169–75 (1989); Szekanecz et al., 42 Agents Actions 159–62 (1994)), secreted cysteine proteases overwhelm residual pericellular cystatin C. The restoration of a physiological balance between the elastolytic cathepsins and inhibitors of these proteases presents a novel therapeutic strategy, especially in aneurysmal disease, where matrix breakdown is dramatic.

In yet another embodiment, the invention provides a method of treating vascular disease in a subject by administering a therapeutically effective amount of TGF-$\beta_1$ to the subject. Similarly, the invention also provides a method of preventing vascular disease or blood vessel elastic laminae breakdown in a subject by administering a prophylactically effective amount of TGF-$\beta_1$ to the subject. The administration of TGF-$\beta_1$ induces secretion of cystatin C. In a particular embodiment, the elastic laminae and collagen breakdown results from inflammation associated with vascular injury.

Cystatin C compositions. In one embodiment, the invention provides a method of treating vascular disease in a subject by administering a therapeutically effective amount of a cysteine proteinase inhibitor to the subject. The invention also provides a method of preventing vascular disease or blood vessel elastic laminae breakdown in a subject by administering a prophylactically effective amount of a cysteine proteinase inhibitor to the subject. The invention also-provides a method of preventing elastic laminae and collagen breakdown resulting from inflammation associated with vascular injury by administering a prophylactically effective amount of a cysteine proteinase inhibitor to the subject.

In various embodiments, the cysteine protease inhibitor can be a cathepsin inhibitor. The cathepsin inhibitor may be structurally similar to cystatin C. By structurally similar to cystatin C is meant that the inhibitor contains a cystatin C active site region. (see for example, Hiltke et al., 78(8) J. Dent. Res. 1401–9 (1999) and Mason et al., 330 (Pt. 2) Biochem J. 833–8 (1998).

For example, the cystatin C inhibitor includes the sequence:
[GSTEQKRV]-Q-[LIVT]-[VAF]-[SAGQ]-G-x-[LIVMNK]-x(2)-[LIVMFY]-x-[LIVMFYA]-[DENQKRHSIV] (SEQ ID NO:3)

Alternatively, the cystatin C inhibitor includes the amino acids comprising the amino terminal β-hairpin loop 1 and β-hairpin loop 2 of cystatin C. Hiltke et al., 78(8) J. Dent. Res. 1401–9 (1999).

Mason et al. found that amino acid substitutions in the N-terminal segment of cystatin C create selective protein inhibitors of lysosomal cysteine proteinases, using site-directed mutagenesis to alter the specificity of human cystatin C. Olsson et al., 1432(1) Biochim Biophys Acta 73–81 (1999) investigated the affinity and kinetics of inhibition of cysteine proteinases by intact recombinant bovine cystatin C. Furthermore, Nycander et al., 422(1) FEBS Lett. 61–4 found that a two-step mechanism of inhibition of cathepsin B by cystatin C due to displacement of the proteinase occluding loop, using stopped-flow kinetics.

The polypeptide sequence for human cystatin C (EMBL locus HSCYSTC 1, Gen Bank Accession No.CAA43856) is MAGPLRAPLLLLAILAVALAVS-PAAGSSPGKPPRLVGGPMDASVEEEGVRRALD FAVGEYNKASNDMYHSRALQVVRARK-QIVAGVNYFLDVELGRTTCTKTQPNLD NCPFH-DQPHLKRKAFCSFQIYAVPWQGTMTLSKSTCQDA (SEQ ID NO:1).

Compositions of cystatin C may be prepared as described in U.S. Pat. Nos. 5,164,295, 5,270,165; and 5,432,264, incorporated herein by reference.

The cysteine protease inhibitor is cystatin C, or functional equivalents or variants of cystatin C, including recombinant forms. The term "cystatin C" means native or recombinant cystatin C, and functional mutants, variants, or truncated forms thereof.

The polypeptide or nucleic acids of the invention need not be identical to the amino acid residue sequence of the cystatin C polypeptide, for example, so long as the polypeptides are able to bind to and inactivate relevant cathepsins. The polypeptide of the invention also includes any analog, fragment or chemical derivative of the cystatin C polypeptide, so long as the polypeptide is functionally active. The term "analog" includes a polypeptide having an amino acid residue sequence substantially identical to the cystatin C polypeptide sequence in which one or more amino acid residues have been conservatively substituted with a functionally similar residue. Peptide equivalents can differ from the cystatin C polypeptide polypeptides by the substitution or modification of side chains or functional groups, without destroying biological function. Modifications can include, for example, additions, deletions, or substitutions of amino acids residues, substitutions with compounds that mimic amino acid structure or functions, and the addition of chemical moieties, such as amino or acetyl groups. An "amino acid residue" is an amino acid formed upon chemical digestion (hydrolysis) of a polypeptide at its peptide linkages. A "fragment" is a polypeptide of the invention having an amino acid residue sequence shorter than 50 amino acids.

The amino acid residues described herein are preferably in the "L" isomeric form. However, residues in the "D" isomeric form can be substituted for any L-amino acid residue, as long as the polypeptides inhibit cathepsins. This definition includes, unless otherwise specifically indicated, chemically modified amino acids, including amino acid analogs (such as penicillamine, 3-mercapto-D-valine), naturally occurring non-proteogenic amino acids (such as norleucine), and chemically synthesized compounds that have properties known in the art to be characteristic of an amino acid. The term "proteogenic" indicates that the amino acid can be incorporated into a protein in a cell through well-known metabolic pathways.

The term "conservative substitution" also includes the use of a chemically derivatized residue in place of a non-derivatized residue provided that such polypeptide displays the requisite activity. "Chemical derivative" refers to a polypeptide of the invention having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. Also included as chemical derivatives are those peptides that contain one or more naturally occurring amino acid derivatives of the twenty standard amino acids. For examples, 4-hydroxyproline may be substituted for proline; 5-hydroxylysine may be substituted for lysine; 3-methylhistidine may be substituted for histidine; homoserine may be substituted for serine; and ornithine may be substituted for lysine.

Some useful modifications are designed to increase the stability of the polypeptide in solution, and therefore serve to prolong half life of the polypeptides in solutions, particularly biological fluids such as blood, plasma or serum, by blocking proteolytic activity in the blood. A polypeptide can have a stabilizing group at one or both termini. Typical stabilizing groups include amido, acetyl, benzyl, phenyl, tosyl, alkoxycarbonyl, alkyl carbonyl, benzyloxycarbonyl and the like end group modifications. Additional modifications include using a "L" amino acid in place of a "D" amino acid at the termini, cyclization of the polypeptide, and amide rather than amino or carboxy termini to inhibit exopeptidase activity.

A polypeptide of the invention may or may not be glycosylated. The polypeptides are not glycosylated, for example, when are produced directly by peptide synthesis techniques or are produced in a prokaryotic cell transformed with a recombinant polynucleotide of the invention. Eukaryotically-produced peptide molecules are typically glycosylated.

TGF-β compositions. The term "TGF-$β_1$" means native or recombinant TGF-$β_1$, and functional mutants, variants, or truncated forms thereof. The sequence of human transforming growth factor-beta, (locus HUMTGFBC accession M60315.1) is
MPGLGRRAQWLCWWWGLLCSCCGPPPLR-PPLPAAAAAAGGQLLGDGGSPGR TEQPPPSPQSSS-GFLYRRLKTQEKREMQKEILSVLGLPHR-PRPLHGLQQPQPPALR QQEEQQQQQQLPRGEPPPGRLKSAP-LFMLDLYNALSADNDEDGASEGERQQSW PHEAASSSQRRQPPPGAAHPLNRK-SLLAPGSGSGGASPLTSAQDSAFLNDADMV MSFVN-LVEYDKEFSPRQRHHKEFKFNLSQIPE-GEVVTAAEFRIYKDCVMGSFKN QTFLISIYQVLQEHQHRDSDLFLLDTRV-
VWASEEGWLEFDITATSNLWVVTPQHN MGLQLSV-
VTRDGVHVHPRAAGLVGRDGPYDKQPFM-
VAFFKVSEVHVRTFRSAS
SRRRQQSRNRSTQSQDVARVSSASDYNS-
SELKTACRKHELYVSFQDLGWQDWII APKGYAANY-
CDGECSFPLNAHMNATNHAIVQTLVHLM-
NPEYVPKPCCAPTKLN
AISVLYFDDNSNVILKKYRNMVVRACGCH (SEQ ID NO:2).

How to make the cystatin C or TGF-β polypeptides of the invention. The polypeptides of the invention can be produced by well known chemical procedures, such as solution or solid-phase peptide synthesis, or semi-synthesis in solution beginning with protein fragments coupled through conventional solution methods, as described by Dugas & Penney, *Bioorganic Chemistry*, 54–92 (Springer-Verlag, New York, 1981). Alternatively, a polypeptide of the invention can be synthesized by using well known methods including recombinant methods and chemical synthesis.

A polypeptide of the invention can be chemically synthesized, for example, by the solid phase peptide synthesis of Merrifield et al., 85J. Am. Chem. Soc. 2149 (1964). Alternatively, a polypeptide of the invention can be synthesized using standard solution methods (see, for example, Bodanszky, *Principles of Peptide Synthesis* (Springer-Verlag, 1984)). Newly synthesized peptides can be purified, for example, by high performance liquid chromatography (HPLC), and can be characterized using, for example, mass spectrometry or amino acid sequence analysis.

The polypeptides of the invention are particularly useful when they are maintained in a constrained secondary conformation. The terms "constrained secondary structure," "stabilized" and "conformationally stabilized" indicate that the peptide bonds comprising the peptide are not able to rotate freely but instead are maintained in a relatively fixed structure. A method for constraining the secondary structure of a newly synthesized linear peptide is to cyclize the peptide using any of various methods well known in the art. For example, a cyclized polypeptide of the invention can be prepared by forming a peptide bond between non-adjacent amino acid residues as described, for example, by Schiller et al., 25 Int. J. Pent. Prot. Res. 171 (1985). Peptides can be synthesized on the Merrifield resin by assembling the linear peptide chain using $N_\alpha$-Fmoc-amino acids and Boc and tertiary-butyl proteins. Following the release of the peptide from the resin, a peptide bond can be formed between the amino and carboxy termini.

A newly synthesized linear peptide can also be cyclized by the formation of a bond between reactive amino acid side chains. For example, a peptide containing a cysteine-pair can be synthesized, with a disulfide bridge can be formed by oxidizing a dilute aqueous solution of the peptide with $K_3Fe(CN)_6$. Alternatively, a lactam such as an ,-((-glutamyl)-lysine bond can be formed between lysine and glutamic acid residues, a lysinonorleucine bond can be formed between lysine and leucine residues or a dityrosine bond can be formed between two tyrosine residues. Cyclic peptides can be constructed to contain, for example, four lysine residues, which can form the heterocyclic structure of desmosine (see, for example, Devlin, *Textbook of Biochemistry* 3rd Edition (1992). Methods for forming these and other bonds are well known in the art and are based on well known rules of chemical reactivity (Morrison & Boyd, *Organic Chemistry*, 6th Edition (Prentice Hall, 1992)).

Recombinant methods of producing a polypeptide of the invention through the introduction of a vector including a polypeptide encoding the peptide into a suitable host cell is well known in the art, such as is described in Sambrook et al., *Molecular Cloning: A Laboratory Manual*, $2^{nd}$ Edition (Cold Spring Harbor Press, 1989). The term "recombinant" refers to the molecular biological technology for combining polynucleotides to produce useful biological products, and to the polynucleotides and peptides produced by this technology. The polynucleotide can be a recombinant construct (such as a vector or plasmid) which contains the polynucleotide encoding the peptide or fusion protein under the operative control of polynucleotides encoding regulatory elements such as promoters, termination signals, and the like. "Operatively linked" refers to a juxtaposition wherein the components so described are in a relationship permitting them to function in their intended manner. A control sequence operatively linked to a coding sequence is ligated such that expression of the coding sequence is achieved under conditions compatible with the control sequences. "Control sequence" refers to polynucleotide sequences which are necessary to effect the expression of coding and non-coding sequences to which they are ligated. Control sequences generally include promoter, ribosomal binding site, and transcription termination sequence. Determinations of the sequences for the polynucleotide coding region that codes for the peptides described herein can be performed using commercially available computer programs, such as DNA Strider and Wisconsin GCG. Owing to the natural degeneracy of the genetic code, the skilled artisan will recognize that a sizable yet definite number of DNA sequences can be constructed which encode the claimed peptides (see, Watson et al., *Molecular Biology of the Gene*, 436–437 (The Benjamin/Cummings Publishing Co., 1987)).

In addition, "control sequences" refers to sequences which control the processing of the peptide encoded within the coding sequence; these can include, but are not limited to sequences controlling secretion, protease cleavage, and glycosylation of the peptide. The term "control sequences" is intended to include, at a minimum, components whose presence can influence expression, and can also include additional components whose presence is advantageous, for example, leader sequences and fusion partner sequences. A "coding sequence" is a polynucleotide sequence that is transcribed and translated into a polypeptide. Two coding polynucleotides are "operably linked" if the linkage results in a continuously translatable sequence without alteration or interruption of the triplet reading frame. A polynucleotide is operably linked to a gene expression element if the linkage results in the proper function of that gene expression element to result in expression of the coding sequence. "Transformation" is the insertion of an exogenous polynucleotide (i.e., a "trangene") into a host cell. The exogenois polynucleotide is integrated within the host genome. A polynucleotide is "capable of expressing" a peptide if it contains nucleotide sequences which contain transcriptional and translational regulatory information and such sequences are "operably linked" to polynucleotide which encode the peptide. A polynucleotide that encodes a peptide coding region can be then amplified, for example, by preparation in a bacterial or viral vector, according to conventional methods, for example, described in Sambrook et al., *Molecular Cloning: A Laboratory Manual*, $2^{nd}$ Edition (Cold Spring Harbor Press, 1989). Expression vehicles include plasmids or other vectors.

The polynucleotide encoding the polypeptide of the invention can be prepared by chemical synthesis methods or by recombinant techniques. The polypeptides can be prepared conventionally by chemical synthesis techniques, such as described by Merrifield, 85 J. Amer. Chem. Soc. 2149–2154 (1963) (see, Stemmer et al., 164 Gene 49 (1995)). Synthetic genes, the in vitro or in vivo transcription and translation of which will result in the production of the protein can be constructed by techniques well known in the art (see Brown et al., 68 Methods in Enzymology 109–151 (1979)). The coding polynucleotide can be generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404).

Alternatively, systems for cloning and expressing polypeptide of the invention include various microorganisms and cells that are well known in recombinant technology. These include, for example, various strains of *E. coli*, Bacillus, Streptomyces, and Saccharomyces, as well as mammalian, yeast and insect cells. Suitable vectors are known and available from private and public laboratories and depositories and from commercial vendors. See, Sambrook et al., *Molecular Cloning: A Laboratory Manual*, $2^{nd}$ Edition (Cold Spring Harbor Press, 1989). See also, PCT International patent application WO 94/01139). These vectors permit infection of patient's cells and expression of the synthetic gene sequence in vivo or expression of it as a peptide or fusion protein in vitro.

Polynucleotide gene expression elements useful for the expression of cDNA encoding peptides include, but are not limited to (a) viral transcription promoters and their enhancer elements, such as the SV40 early promoter, Rous sarcoma virus LTR, and Moloney murine leukemia virus LTR; (b) splice regions and polyadenylation sites such as those derived from the SV40 late region; and (c) polyadenylation sites such as in SV40. Recipient cells capable of expressing the gene product are then transfected. The transfected recipient cells are cultured under conditions that permit expression of the gene products, which are recovered from the culture. Host mammalian cells, such as Chinese Hamster ovary cells (CHO) or COS-1 cells, can be used. These hosts can be used in connection with poxvirus vectors, such as vaccinia or swinepox. Suitable non-pathogenic viruses that can be engineered to carry the synthetic gene into the cells of the host include poxviruses, such as vaccinia, adenovirus, retroviruses and the like. A number of such non-pathogenic viruses are commonly used for human gene therapy, and as carrier for other vaccine agents, and are known and selectable by one of skill in the art. The selection of other suitable host cells and methods for transformation, culture, amplification, screening and product production and purification can be performed by one of skill in the art by reference to known techniques (see, e.g., Gething & Sambrook, 293 Nature 620–625 (1981)).

Another preferred system includes pSec Tag2 expression vectors (Invitrogen, San Diego, Calif.). These 5.2 kb mammalian expression vectors offer features for secretion, purification, and detection of fusion proteins. The vectors carry the secretion signal from the V-J2-C region of the mouse Ig 6-chain for efficient secretion of recombinant proteins from a variety of mammalian cell lines. The vectors also carry a C-terminal tag sequence that allows rapid purification and detection of fusion proteins. Recombinant proteins are fused to six histidine residues to allow one-step purification (which can be removed following purification) and the anti-myc epitope for rapid detection.

When produced by conventional recombinant means, peptide can be isolated either from the cellular contents by conventional lysis techniques or from cell medium by conventional methods, such as chromatography (see, e.g., Sambrook et al., *Molecular Cloning: A Laboratory Manual*, $2^{nd}$ Edition (Cold Spring Harbor Press, 1989). Methods for recovering an expressed recombinant polypeptide are well known in the art and include fractionation of the protein-containing portion of the culture using well known biochemical techniques. For instance, the methods of gel filtration, gel chromatography, ultrafiltration, electrophoresis, ion exchange, affinity chromatography and the like, such as are known for protein fractionations, can be used to isolate the expressed proteins found in the culture. In addition, immunochemical methods, such as immunoaffinity, immunoadsorption and the like can be performed using well known methods.

Pharmaceutical compositions. The invention provides pharmaceutical compositions comprising a therapeutically effective dose of the polypeptide an nucleic acids of the invention in a pharmaceutically acceptable excipient, for administration to a subject, such as a human patient. The term "therapeutically effective amount" means the dose needed to effectively treat cellular infiltration and attendant cytokine network alterations associated with a variety of inflammatory diseases and injuries. For purposes of the invention, the terms "treat" and "treatment" include preventing, inhibiting, reducing the occurrence of, or ameliorating the physiological effects of the inflammatory condition treated.

The term "pharmaceutically acceptable excipient" includes any solvents, dispersion media, antibacterial and antifungal agents, microcapsules, liposomes, cationic lipid carriers, isotonic and absorption delaying agents and the like which are not incompatible with the active ingredients. The formulation of pharmaceutical compositions is generally known in the art; reference can conveniently be made to *Remington's Pharmaceutical Sciences*, $17^{th}$ Edition (Mack Publishing Co., Easton, Pa.) Thus, the pharmaceutical compositions can comprise a suitable application medium, such as a gel, salve, lotion, colloid or powder, aqueous solutions such as physiologically buffered saline or other solvents or vehicles such as glycols, glycerol, oils such as olive oil or injectable organic esters. Pharmaceutical compositions can be prepared as injectables, either as liquid solutions or suspensions. The preparation can also be emulsified.

Physiologically acceptable excipients include, for example, carbohydrates, such as glucose, sucrose or dextrans, antioxidants, such as ascorbic acid or glutathione, chelating agents, low molecular weight proteins or other stabilizers or excipients. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents that enhance the effectiveness of the active ingredient. A polypeptide can also be formulated into the pharmaceutical composition as neutralized pharmaceutically acceptable salt forms. Pharmaceutically acceptable salts include the acid addition salts (formed with the free amino groups of the polypeptide or antibody molecule) that are formed with inorganic acids such as, for example, hydrochloric or phosphoric acids, or such organic acids as acetic, tartaric, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The pharmaceutical forms suitable for infusion include sterile aqueous solutions or dispersions and sterile powders for the extemporaneous preparation of sterile injectable solutions or dispersion. The form is fluid to the extent that easy syringability exists. Typical excipients include a solvent or dispersion medium containing, for example, water buffered aqueous solutions (i.e., biocompatible buffers), ethanol, polyols such as glycerol, propylene glycol, polyethylene glycol, suitable mixtures thereof, surfactants, or vegetable oils. Sterilization can be accomplished by any art-recognized technique, including but not limited to filtration or addition of antibacterial or antifungal agents, for example, paraben, chlorobutanol, phenol, sorbic acid or thimerosal. Further, isotonic agents such as sugars or sodium chloride may be incorporated in the pharmaceutical compositions. Prevention against microorganism contamination can be achieved through the addition of various antibacterial and antifungal agents.

Methods of administration. The cystatin C and cystatin C expression-inducing compositions (e.g. TGF-$\beta_1$) of the invention may be administered to a subject in any manner known to those of skill in the art. In particularly preferred embodiments, the administration of cystatin C blocks about 50% or greater of IFN-$\gamma$-induced cathepsin S activity, and the administration of TGF-$\beta_1$, blocks about 75% of IFN-$\gamma$-induced cathepsin S activity.

The polypeptides of the invention can be administered in any way that is medically acceptable which may depend on the disease condition or injury being treated. For example the inhibitors of the invention may be administered locally in a solution form at a site of vascular injury through a catheter port or as a coating on the surface of a catheter, e.g., a perfusion catheter or the balloon portion of a catheter used for balloon Possible administration routes include injections, by parenteral routes such as intravascular, intravenous, intraarterial, subcutaneous, intramuscular, intratumor, intraperitoneal, intraventricular, intraepidural or others, as well as oral, nasal, ophthalmic, rectal, topical, or by inhalation. The compositions may also be directly applied to tissue surfaces during surgery. For example the inhibitors can be administered before, during or after angioplasty. In addition, the inhibitors can be administered as a coating on a stent that is implanted at the site of a vascular lesion, e.g., an aneurysm. (see e.g., U.S. Ser. No. 5,902,266) Sustained release administration is also specifically included in the invention, by such means as depot injections or erodible implants. Administration can also be intra-articularly, intrarectally, intraperitoneally, intramuscularly, subcutaneously, or by aerosol inhalant in order to prevent particular inflammatory and immune reactions associated with such areas of the body. Where treatment is systemic due, for example, to the presence in the subject of metastatic tumor cells, the composition can be administered orally or parenterally, such as intravenously, intramuscularly, subcutaneously, intraorbitally, intracapsularly, intraperitoneally or intracisternally.

The pharmaceutical compositions are conventionally administered intravenously, as by injection of a unit dose. The term "unit dose" when used in reference to a pharmaceutical composition of the invention refers to physically discrete units suitable as unitary dosages for humans, each unit containing a predetermined quantity of active material calculated to produce the desired therapeutic effect.

The quantity to be administered depends on the subject to be treated, capacity of the subject to utilize the active ingredient, and degree of inhibition of receptor-ligand binding desired. Precise amounts of active ingredient required to be administered depend on the judgment of the practitioner and are peculiar to each individual. However, suitable dosage ranges are of the order of one to several mg of active ingredient per individual per day and depend on the route of administration. Suitable regimes for initial administration and booster shots are typified by an initial administration followed by repeated doses at one or more hour intervals by a subsequent injection or other administration.

Alternatively, continuous intravenous infusion sufficient to maintain therapeutically effective concentrations in the blood are contemplated. For a polypeptide of the invention, therapeutically effective blood concentrations are in the range of about 1 nM to 1 mM, preferably from 50 nM to 100 $\mu$M.

Whenever, the polypeptides of the invention are used for promoting attachment of cells, such compositions will typically have a higher concentration than those taken internally.

Dosage. The precise therapeutically effective amount of polypeptide of the invention used in the methods of this invention applied to humans can be determined by the ordinarily skilled artisan with consideration of individual differences in age, weight, extent of cellular infiltration by inflammatory cells and condition of the patient. The pharmaceutical preparation of the invention should be administered to provide an effective concentration of 1 nM to 1 mM, preferably from 50 nM to 100 $\mu$M. In preferred embodiments, the therapeutically and prophylactially effective amounts of cystatin C comprise about 10–500 ng/ml, and the therapeutically and prophylactially effective amounts of TGF-$\beta_1$ comprise about 1–10 ng/ml. In particularly preferred embodiments, the therapeutically and prophylactically effective amounts of cystatin C and TGF-$\beta_1$ comprise about 50 ng/ml and about 1 ng/ml, respectively.

The amount of the inhibitor in the pharmaceutical composition of the present invention will depend upon the nature and severity of the condition being treated, and on the nature of prior treatments which the patient has undergone. Ultimately, the attending physician will decide the amount of inhibitor with which to treat each individual patient. Initially, the attending physician will administer low doses of inhibitor and observe the patient's response. Larger doses of inhibitor may be administered until the optimal therapeutic effect is obtained for the patient, and at that point the dosage is not generally increased further. It is contemplated that the various pharmaceutical compositions used to practice the method of the present invention should contain about 0.1 $\mu$g to about 100 mg of inhibitor per kg body weight. Preferred ranges include is a dosages of about 100 $\mu$g to 6 mg, and 20 $\mu$g to 500 $\mu$g per kg of body weight.

The duration of intravenous therapy using the pharmaceutical composition of the present invention will vary, depending on the severity of the disease being treated and the condition and potential idiosyncratic response of each individual patient. Ultimately the attending physician will decide on the appropriate duration of intravenous therapy using the pharmaceutical composition of the present invention.

The total effective amount of a polypeptide of the invention can be administered to a subject as a single dose, either as a bolus or by infusion over a relatively short period of time, or can be administered using a fractionated treatment protocol, in which the multiple doses are administered over a more prolonged period of time.

It is especially advantageous to formulate parenteral compositions in dosage unit form for ease of administration and uniformity of dosage. "Dosage unit form" refers to physically discrete units suited as unitary dosages for the mammalian subjects to be treated; each unit containing a predetermined quantity of active material calculated to produce the desired therapeutic effect in association with the required pharmaceutical excipient. A pharmaceutical composition typically contains an amount of at least 0.1 weight % of active ingredient, i.e., a polypeptide or antibody of this invention, per weight of total pharmaceutical composition. A weight % is a ratio by weight of active ingredient to total composition. Thus, for example, 0.1 weight % is 0.1 grams of polypeptide per 100 grams of total composition.

In vitro diagnostics. Patients with progressing atherosclerosis exhibit low circulating cystatin C, even though they may not present gross aortic morphological change. This observation represents a novel means of diagnosing patients at risk of, or with, progressing vascular disease. In one embodiment, the invention provides a method of diagnosing a patient at risk of, or with, vascular injury by detecting low circulating levels of cystatin C in blood serum. In a particularly preferred embodiment the low cystatin C level is about 50% or less of the control cystatin C level (where the ratio is determined using levels defined as the mean±2 standard deviations), and in another particularly preferred embodiment, the vascular injury comprises atherosclerosis (see, Randers et al., Clin. Chem. Lab Med., 37(4):389–95 (1999). For example, the normal patient control cystatin C level in EXAMPLE III is 1.303±1.064 µg/ml. This detection may be accomplished by any method well known in the art, for example, ELISA, as discussed above.

Therapeutic use. Vascular diseases within the scope of the invention include, but are not limited to, atherosclerosis, myocardial infarction, arterial aneurysms, including abdominal aortic aneurysm, inflammatory diseases, including giant cell arteritis, vascular tumors, and tumor-induced vascular lesions.

We have discovered a downward skewing of circulating cystatin C levels among subjects with dilated aortas and the severe depletion of cystatin C within atherosclerotic and aneurysmal lesions. This downward skewing indicate a common response to similar local and systemic changes in the cytokine milieu in these settings. Numerous studies have documented evidence of increased local and systemic markers of inflammation, e.g. the cytokine IL-6 and the acute phase reactant, C-reactive protein, in atherosclerosis and aneurysmal disease (Szekanecz et al., 42 Agents Actions 159–62 (1994); Ridker et al., 46 J. Investig. Med. 91–95 (1998)). Additionally, both decreased systemic active TGF-$\beta_1$ and local resistance to TGF-$\beta_1$ activity have been reported in atherosclerosis by Grainger et al., 1 Nature Med. 74–79 (1995); and McCafrey et al., 100 J. Clin. Invest. 2182–88 (1997)

The method of the invention inhibits the activity of cathepsin K. Cathepsin K is the most potent mammalian elastase yet described (see, Bossard et al., 271 J. Biol. Chem. 12517–524 (1996); Bromme et al., 271 J. Biol. Chem. 2126–32 (1996)). Cathepsin K also has collagenolytic activity (Kafienah et al., 331 Biochem J. 727–32 (1998)).

The overexpression of cathepsin S and cathepsin K in atherosclerotic lesions compared to normal arteries has been demonstrated by Shi et al., 357 FEBS Lett. 129–34 (1995). Also, macrophages and smooth muscle cells in atherosclerotic plaques express cathepsins S and K (Sukhova et al., 102 J. Clin. Invest. 576–83 (1998)). In the presence of pro-inflammatory cytokines found in atheroma, cultured vascular smooth muscle cells secrete active cathepsin S capable of degrading extracellular elastin. Monocyte-derived macrophages also degrade elastin through release of active cathepsins (see, Reedy et al., 92 Porch. Natl. Acad. Sci. 3849–853 (1995)).

This degradative mechanism is reminiscent of the bone macrophage, osteoclasts. Indeed, in osteoclasts, cathepsin K appears to be the major protease involved in extracellular matrix metabolism necessary for normal bone growth and remodeling (Bossard et al., 271 J. Biol. Chem. 12517–524 (1996)). Deficiency of this enzyme results in accumulation of bone matrix mostly around, rather than in, osteoclasts, consistent with the primary site of action of cathepsin K in the pericellular space (Gelb et al., 273 Science 1236–38 (1996)). Together, these studies indicate that under some conditions macrophages utilize certain elastolytic cathepsins to remodel extracellular matrix.

Thus, the invention is useful for preventing, inhibiting, or ameliorating inflammatory and immune reactions associated with various injury and disease conditions. The term "subject" means any mammal to which the compositions of the invention may be administered. Subjects specifically intended for treatment with the compositions and methodologies of the invention include humans.

Inflammation is the body's reaction to injury and infection. Three major events are involved in inflammation: (1) increased blood supply to the injured or infected area; (2) increased capillary permeability enabled by retraction of endothelial cells; and (3) migration of leukocytes out of the capillaries and into the surrounding tissue (hereinafter a referred to as cellular infiltration; see, Roitt et al., Immunology, (Grower Medical Publishing, New York, 1989). Inflammatory cells and mediators including leukocytes, cytokines, oxygen radicals, complement and arachidonate metabolite damage capillary endothelium and allow fluid and protein to leak across capillaries. Inflammation also involves the release of inflammatory mediators (inflammatory cytokines, platelet activating factor, complement, leukotrienes, oxygen metabolites, and the like). Inflammatory responses are thus induced both at the original site of trauma and also in the vasculature and remote vascularized sites. Neutrophils, eosinophils, mast cells, lymphocytes and macrophages contribute to the inflammatory response. Neutrophils contribute by generating oxidants or releasing proteases that damage the microvasculature or adjacent tissue. Cell death and tissue damage due to complement and inflammatory cell mechanisms lead to organ failure or decreased organ function. The activation of mediators by a local injury can also cause a remote injury to highly vascularized organs.

The details of one or more embodiments of the invention are set forth in the accompanying description above. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The following EXAMPLES are presented in order to more fully illustrate the preferred embodiments of the invention. These examples should in no way be construed as limiting the scope of the invention, as defined by the appended claims.

EXAMPLE 1

Immunostaining to Show Cystatin C Expression in Normal and Atherosclerotic Human Arterial Tissue This EXAMPLE shows decreased expression of cystatin C in atherosclerotic plaques and abdominal aortic aneurysm (AAA) by the immunostaining of normal vessels and atherosclerotic plaques.

Plaques and normal vessels were immunostained with rabbit anti-human cystatin C polyclonal antibodies to examine if the lesions also exhibit altered levels of their endogenous inhibitor cystatin C. Slides for immunostaining were prepared as follows: Serial cryostat sections (6 μm) of human atherosclerotic plaques from coronary and carotid arteries, aortic aneurysms, as well as nonatherosclerotic arteries (carotids from autopsies and aortas from cardiac transplantation donors were fixed in acetone (−20° C., 5 minutes), air dried, and stained by an avidin-biotin-peroxidase method as previously described (Sukhova et al., 102 J. Clin. Invest. 576–83 (1998)). Tissue sections were treated with 0.3% hydrogen peroxide to inhibit endogenous peroxidase activity and incubated with primary antibodies diluted in PBS supplemented with 4% species-appropriate normal serum. The subsequent processing was performed according to the manufacturer's recommendations (Universal Dako LSAB kit, peroxidase; DAKO Co., Carpinteria, Calif., USA). The reaction was visualized with 3-amino-9-ethylcarbazole (AEC; Sigma Chemical Co., St. Louis, Mo., USA). Sections were counterstained with Gill's hematoxylin solution (Sigma Chemical Co.). Cell types were identified with monoclonal anti-muscle actin HHF-35 (Enzo Diagnostics Inc., Farmingdale, N.Y., USA) or monoclonal anti-human CD68 (macrophages).

Normal arteries exhibit abundant cystatin C staining. However, atherosclerotic plaques show little immunoreactive cystatin C. Macrophages and smooth muscle cells in the developing plaques were identified by immunostaining plaques with mouse anti-human CD68 (macrophage-specific) and mouse anti-human-actin (smooth muscle cells specific) antibodies. As expected, vivid CDG8 staining is found at the lipid core and shoulder areas of the plaque whereas a-actin staining was found mostly in the fibrous cap. The specificity of immunohistochemistry was confirmed using nonimmune rabbit serum.

Surprisingly, the level of cystatin C in atherosclerotic plaques correlates with disease progression. Early stages of plaque development (fatty streaks) show very little immunodetectable cystatin C, whereas smooth muscle cells of underlying media (-actin positive) demonstrate stronger staining for cystatin C. Abdominal aortic aneurysm displays a similar lack of cystatin C staining, as well as increased cathepsin S immunostaining. Thus, abdominal aortic aneurysm and atherosclerotic plaques contain scant cystatin C.

EXAMPLE 2

Immunoblotting to Show Cystatin C Expression in Normal and Atherosclerotic Human Arterial Tissue Immunoblotting was performed with normal arteries, atherosclerotic plaques, and aortic aneurysms using rabbit polyclonal antibodies against cystatin C, cathepsin S or cathepsin K. Both atherosclerotic plaques and aortic aneurysms demonstrated markedly decreased cystatin C antigen, whereas both cathepsin S and cathepsin K were increased in aneurysmal aortae.

Protein extracts of atherosclerotic artery, aneurysmal tissue, and normal control vessel were examined by immunoblotting with cathepsin and cystatin C antibodies. Western blot analysis was performed as follows: Frozen atherosclerotic plaques, abdominal aortic aneurysm aortas, and normal arteries were pulverized and lysed into buffer containing 1% Triton X-100, 40 mM sodium acetate, and 1 mM EDTA, pH 5.0. After incubation at 37° C. for 1 hr., lysate protein concentrations were determined using Bio-Rad Dc protein assay kit according to the manufacturer (Bio-Rad Dc., Bio-Rad Laboratories, Inc., Hercules, Calif., USA). Thirty micrograms of protein from each sample was separated on SDS-PAGE, blotted onto nitrocellulose filter, and probed with rabbit anti-human cystatin C (1:1000, DAKO Corporation) or human cathepsin S (1:1000).

Human sapheneous vein smooth muscle cells were cultured in Swell plates in Dulbecco's Modification of Eagle's Medium (DMEM) containing 10% fetal bovine serum (FBS) until confluent. Cells were then cultured in serum free DMEM for 24 hours followed by stimulation with INF-γ (500 units/ml) for additional 24 hours in the presence or absence of 10 ng/ml TGF-β1. Culture medium was then collected and centrifuged at 16000×g for 10 min. Proteins were precipitated with 20% trichloroacetic acid on ice for 30 min. followed by repeat centrifugation. The protein pellet was briefly washed with 100% ethanol and resuspended in electrophoresis sample buffer smooth muscle cells were lysed directly into sample buffer after two washes with 1×PBS. Both cell lysates and proteins from culture medium were separated on SDS-PAGE for immunoblot analysis with antibodies against human cathepsin S and cystatin C as described above. All Western blots were developed with Western Blot Chemiluminescence Reagent (NEN Life Science Products, Inc., Boston, Mass., USA).

Similar to the findings with immunostaining, immunoblot analysis with cystatin C antibodies indicates a dramatic decrease of 13 kDa cystatin C antigen in atherosclerotic plaque extracts, as well as abdominal aortic aneurysm extracts, as compared with normal arteries. Cathepsins S and K expression in abdominal aortic aneurysm extracts is increased, consistent with previously reported data for atherosclerotic plaques (Sukhova et al., 102 J. Clin. Invest. 576–83 (1998)).

These findings evidence a disturbed balance between proteases and anti-proteases involving elastolytic and collagenolytic cysteine proteases in these diseased vessel walls.

EXAMPLE 3

Correlation Between Abdominal Aortic Aneurysm Aorta Diameter and Serum Cystatin C Levels A cohort of 4 patients referred to an outpatient cardiology clinic for echocardiographic testing underwent measurements of carotid artery intimal to medial thickness (IMT) ratios and aortic diameter. Correlations between these measurements and circulating indices of inflammation in this cohort have been previously reported (Rhode et al., 18 Arterioscler. Thromb. Vasc. Biol. 1765–70 (1998)). Serum cystatin C levels in these patients were measured using a cystatin C enzyme-linked immunoassay (ELISA). This method has been previously used to quantify cystatin C levels in human gingiva (Skaleric et al., 34 Arch. Oral. Biol. 301–305 (1989); Shimode et al., 22 Stroke 860–66 (1991); Ishiguro et al., 8 Hybridoma 303–13, (1989)).

The patient population was as follows: Outpatients older than 50 years of age, referred to the Noninvasive Cardiac Laboratory of the Brigham and Women's Hospital for a transthoracic echocardiogram, were invited to participate in a study examining markers of vascular disease (Rhode et al., 18 Arterioscler. Thromb. Vasc. Biol. 1765–70 (1998)). Patients with a clinical history consistent with active infection, systemic inflammatory disease, heart transplant or those taking corticosteroids were excluded. Overall, 122 eligible patients agreed to participate and constituted the study population. Ultrasound evaluations were performed by two experienced ultrasonographers, using commercially available equipment (Hewlett Packard Sonos 2500, Hewlett Packard Medical Products, Andover, Mass., USA) and a 2.7/3.5 MHz phase-array transducer (for the aorta) or a 5.5/7.0 MHz linear transducer (for the carotid imaging) as described elsewhere (Rhode et al., 19 Arterioscler. Thromb. Vasc. Biol. 1695–1699 (1999)). Before the imaging procedures, individual data concerning atherosclerosis risk factors, prior cardiovascular history and other co-morbidities were obtained. The protocol was reviewed and approved by the Human Research Committee of the Brigham and Women's Hospital and informed consent was obtained for all patients.

Among these subjects, 8 patients were identified with abdominal aortic dilatation as defined with periumbilical aorta diameter larger than 2.5 cm. Serum samples from all patients were collected and used for cystatin C ELISA as described by Skaleric et al., 34 Arch. Oral. Biol. 301–305 (1989); Shimode et al., 22 Stroke 860–66 (1991); Ishiguro et al., 8 Hybridoma 303–13 (1989)). Briefly, 96-well immunosorb plates (NUNC Co.) were coated with cystatin C polyclonal IgG (10 µg/ml, Cortex) in NaHCO3, pH8.2 overnight at 4° C. After wash and 3% BSA blocking, plates were incubated with diluted human serum samples and incubated for another overnight at 4° C. Cystatin C monoclonal antibodies (1 µg/ml) were used as detecting antibody followed with peroxidase conjugated goat anti-mouse IgG/IgM (1:1000, KPL). ELISA plates were developed with OPD (Sigma). Recombinant cystatin C was used as standard of each plate.

Cystatin C expression in decreased in atherosclerotic plaques and fatty streaks as compared to normal arteries.

No significant correlation between IMT and cystatin C levels was apparent. However, a significant negative correlation of abdominal aortic diameters with serum cystatin C levels was observed (FIG. 1) (P<0.0.03, R=0.203). The correlation remained significant when aortic diameter was corrected for body surface area and when cystatin C was normalized to serum creatinine, glomerular filtration being a known determinant of cystatin C levels (Kyse-Andersen et al., 40 Clin. Chem. 1921–26 (1994)).

All patients with dilated aortas had relatively low circulating cystatin (0.516±0.233 µg/ml as compared to normal patients 1.303±1.064 µg/ml; see FIG. 1), although the number of patients with frankly dilated aortas (>2.5 cm) is small. As a group these subjects had significantly lower serum cystatin C levels than that of subjects with aortic diameters <2.5 cm (P<.0.03, Mann-Whitney). There is no significant association of cystatin C with age, race, sex, history of smoking, diabetes, myocardial infarction, revascularization, or lipoprotein levels. Hence, cystatin C levels contribute to progression of vascular remodeling, consistent with significantly lower cystatin C levels among subjects with dilated aortas. Additionally, cystatin C exerts a protective (i.e. preventative) effect against matrix breakdown (FIG. 1).

EXAMPLE 4

Figure 2:
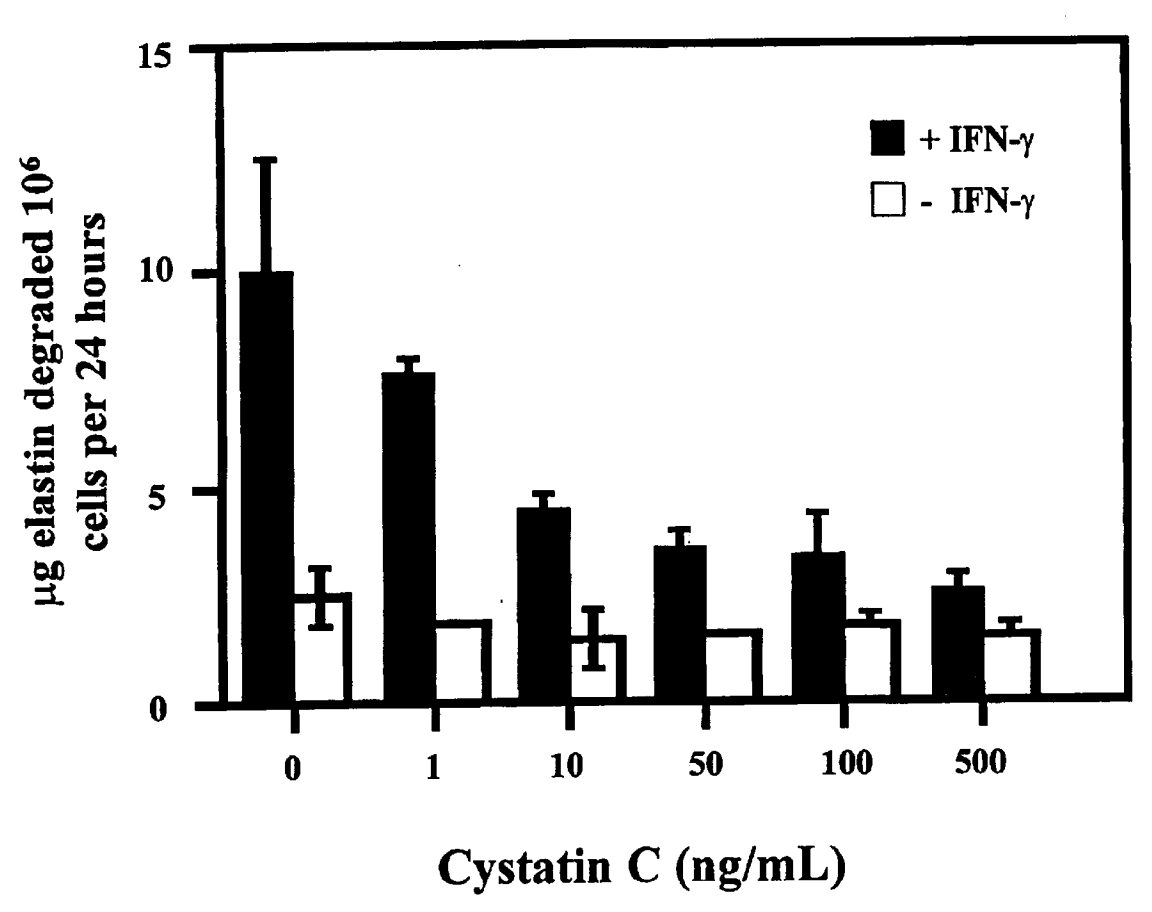

Cystatin C Expression and Regulation of Vascular Smooth Muscle Cells Elastolytic Activity Prior studies documenting the capacity of macrophages to use cysteine proteases to degrade elastin found macrophage elastolytic activity to be insensitive to the presence of pericellular serum protease inhibitors (Reedy et al., 92 Porch. Natl. Acad. Sci. 3849–853 (1995); Chapman et al., 74 J. Clin. Invest. 1693–700 (1984)). Given the marked reduction of cystatin C in atherosclerotic and aneurysmal lesions and the clinical correlation in EXAMPLES 1–3, the influence of cystatin C on the elastolytic activity of cultured vascular smooth muscle cells was examined. Vascular smooth muscle cells were stimulated with IFN-γ (500 units/ml) for 24 hours to augment cathepsin S-dependent elastase activity (Sukhova et al., 102 J. Clin. Invest. 576–83 (1998)). In co-cultures with insoluble elastin, the addition of as little as 10 ng/ml of recombinant cystatin C inhibits elastin degradation (FIG. 2). Higher concentrations of cystatin C block >75% of the IFNγ-induced activity, confirming that smooth muscle cells elastase activity depends largely on elastolytic cysteine proteases.

The regulation of cystatin C expression in smooth muscle cells was further tested using a cytokine previously reported to induce other classes of protease inhibitors, TGF-$\beta_1$ (Buisson et al., 12 FASEB J. 1683–91 (1998); Cao et al., 36 Invest. Orphthalmol. Vis. Sci. 1411–19 (1995); Su et al., 70 J. Cell. Biochem. 517–27 (1998)).

Total RNAs were isolated from control and IFN-γ-stimulated smooth muscle cells for Northern blot analysis. Northern blot analysis was performed as follows: After INF-γ and TGF-β1 treatments, 1.5×10$^7$ smooth muscle cells were lysed in 5 ml of guanidium. isothiocyanate (GTC) lysis buffer for RNA preparation as described (Sukhova et al., 102 J. Clin. Invest. 576–83 (1998)). Twenty micrograms of total RNA from smooth muscle cells were separated on 1.2% agarose gel and blotted on Zeta-Probe GT blotting membrane (Bio-Rad Laboratories, Inc.). A human cystatin C probe was generated by polymerase chain reaction using cystatin C cDNA. The 500 bp cystatin C cDNA fragment and cathepsin S cDNA probe (Sukhova et al., 102 J. Clin. Invest 576–83 (1998)) were labeled with [$^{32}$P]-dCTP and purified with NENSORB 20 column (NEN Life Science Products, Inc.) before hybridizing as previously described (Sukhova et al., 102 J. Clin. Invest. 576–83 (1998)).

The elastase assay was performed as follows: Smooth muscle cells were cultured on 24-well plates in 10% FBS DMEM until 100% confluence (5×10$^5$ cells/well). Cells were then cultured in serum free DMEM for 24 hr before stimulation with INF-γ (500 Units/ml) and/or TGF-$\beta_1$ (1–25 ng/ml). Both stimulated and non-stimulated smooth muscle cells were incubated with 300 µg [$^3$H]-elastin (bovine ligament elastin, 1300 cpm/µg, Elastin Products Inc.) as previously described (Sukhova et al., 102 J. Clin. Invest. 576–83 (1998)) for 3 days at 37° C. The inhibitory effect of cystatin C was examined by incubating smooth muscle cells with recombinant cystatin C (0–500 ng/ml) or rabbit anti-human cystatin C IgG (100 µg/ml, Cortex Biochem, San Leandro, Calif., USA). Culture media were then collected by centrifugation at 16,000×g for 15 min. The digested elastin radioactivity was counted using 200 µl of medium and the data presented as µg elastin degraded per 10$^6$ cells in 24 hours.

As expected, cathepsin S mRNA is markedly increased in stimulated cells as compared with controls.

Surprisingly, the level of cystatin C mRNA was unchanged, consistent with the constitutive nature of the cystatin C promoter (Olafsson, 55 Scand. J. Clin. Lab. Invest. 597–607 (1995)).

Figure 3:
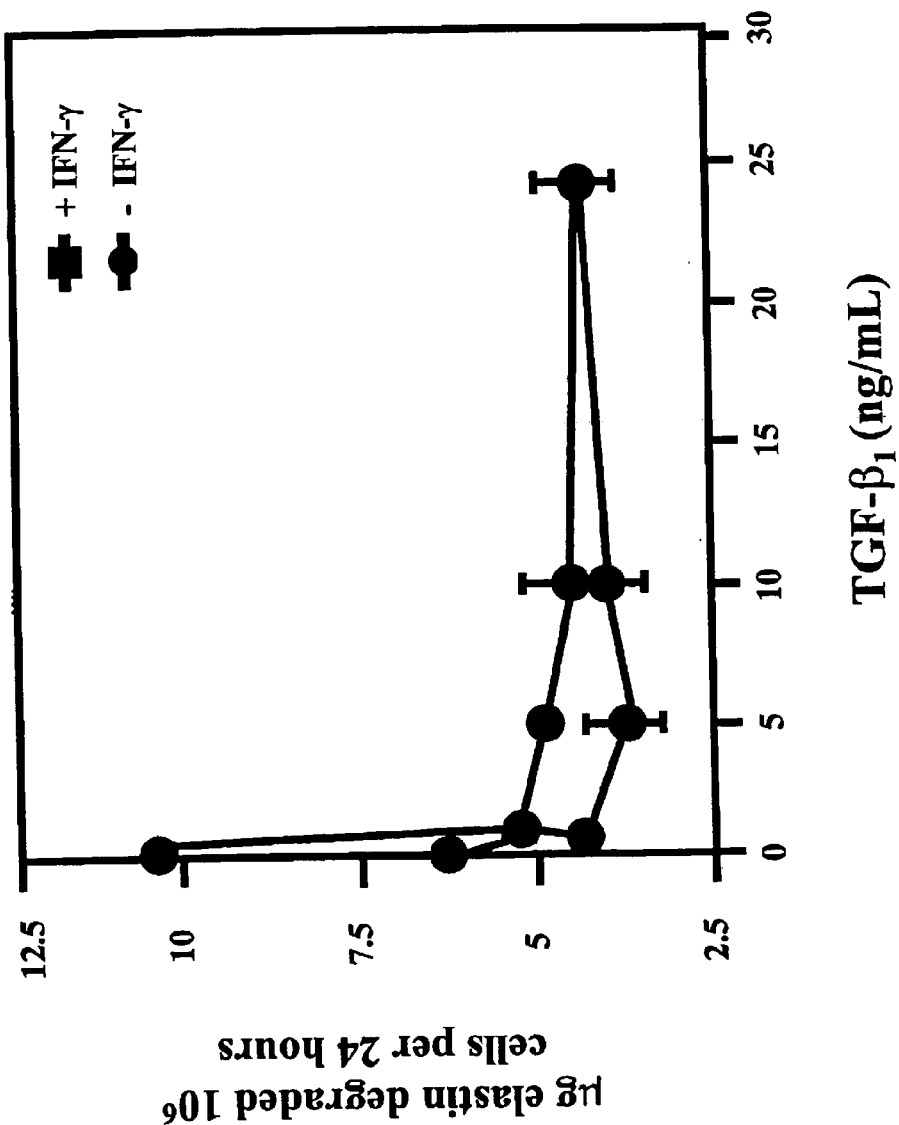
FIG. 3 is a graph showing that TGF-$\beta_1$ blocks smooth muscle cells elastase activity. Interferon-stimulated smooth muscle cells were co-cultured with elastin as above in the presence of increasing amounts of TGF-$\beta_1$ and elastin degradation quantified after 72 hrs.

TGF-$\beta_1$ (5 ng/ml) does not change the level of cathepsin S mRNA or protein, or cystatin C mRNA. However, TGF-$\beta_1$ markedly increases the level of secreted cystatin C. Cystatin C biosynthesis increases as little as one hour after exposure of smooth muscle cells to TGF-$\beta_1$. Consistent with this observation, as little as 1 ng/ml of recombinant TGF-$\beta_1$ almost completely blocks the elastase activity of IFN-$\gamma$-stimulated smooth muscle cells (see, FIG. 3). Thus, cytokine-induced smooth muscle cells elastase activity depends on pericellular cystatin C levels and TGF-$\beta_1$ can induce cystatin C secretion.

In summary, TGF-$\beta_1$ stimulates smooth muscle cells cystatin C secretion while IFN-$\gamma$ induces cathepsin S mRNA and secretion of active cathepsin S, but has no effect on cystatin C secretion.

EXAMPLE 5

In Vivo Suppression of Cathepsin Activity by Cystatin C

The ability of cystatin C to inhibit the activity of cathepsin S and K in vivo is studied using well known atherosclerosis animal models (see,; Purcell-Huynh et al., 95 J. Clin. Invest. 2246–257 (1995); Fruebis et. al., 94J. Clin. Invest. 392–98 (1994); van Ree et al., 305 Biochem J. 905–11 (1995); Masucci et al., 275 Science 391–394 (1997); Chowdhury et al., 254 Science 1802–805 (1991); Tangirala et al., 36 J. Lipid Res. 2320–328 (1995); Ishibashi et al. 93 J. Clin. Invest. 1885–893 (1994)).

In particular, the LDLR$^{-/-}$ mouse model of Litchman et al., 154 FASEB J. 896 (1997) is used, in which atherosclerotic lesion formation in these mice are initiated in a defined fashion by dietary manipulation. Male mice are used, because female mice are not as responsive to diet-induced atherogenesis. Systemic administration of the cathepsins S and K inhibitor cystatin C during the period of atherogenesis are carried out, and animals are sacrificed, and their hearts and aortas collected. Aortae from both cystatin C treated and untreated mice are analyzed with immunohistochemistry to quantify lesional development as above in EXAMPLE 1.

Also, the LDLR$^{-/-}$ mice are manipulated with cathepsin S and cathepsin K transgents. Mouse cathepisn S and K cDNAs driven by the mouse macrophage scavenger receptor promoter are used to generate a transgenic mouse. Overexpression of cathepsins S and K in LDLR –/– mouse is performed as follows: Both mouse cathepsin S and cathepsin K cDNAs are subcloned, respectively, into the 3'-end of mouse macrophage scavenger receptor, a promoter which has been shown to drive gene expression in tissue macrophages under the pathologic circumstance of atheroma formation by Tangirala et al., 36 J. Lipid Res. 2320–2328 (1995). The entire construct containing cathepsin S/K and the promoter is removed from the cloning vector and the purified DNA used to inject four-cell stage oocytes (C57 b/6) (20 $\mu$g per injection). The founder mice and the following progenies are characterized with tail DNA southern blot analysis with cathepsin cDNA probes. Crossbreeding of transgenic cathepsin S/K mice with LDLR$^{-/-}$ mice is carried out in an animal facility. The homozygosity for cathepsin S/K transgene and LDLR–/– alleles is tested with tail DNA southern blot analysis.

A strong promoter is required for cathepsin overexpression. We have found that mutations at the 3'-end of the original 4.5 kb mouse scavenger promoter can increase the reporter gene expression 100–1000-fold.

Coexpression and overexpression of both cathepsins in this transgenic mouse are verified by Southern and Western blot analyses and crossbreeding with LDLR$^{--}$ mice. Coexpression and overexpression of both cathepsins in this transgenic line will induce atherogenesis, and the inhibitory and protective effect of cystatin C administration can be demonstrated by immunohistochemical comparison, as discussed above in EXAMPLE 1.

Alternatively, acute vascular injury may be created by placement of a nonconstrictive cuff around the mouse femoral artery, which results in smooth muscle cells migration, proliferation, and neointima formation. Briefly, mice are anesthetized on day 0 with nembutal and ketamine (0.04 mg/g for each). Under sterile conditions the femoral artery is dissected free and loosely sheathed with a nonocclusive, flexible cuff made of a polyethylene tube (3.0 mm long PE-90, 0.86 mm inner diameter and 1.27 mm outer diameter, Becton Dickinson & Co.) which may then be ligated with a 5–0 silk thread. The wound is irrigated with saline, incision closed with running 3.0 silk suture, and topical antibiotic ointment applied. After recovery from anesthesia, the animals are given a standard diet and water ad libitium. Post-operative analgesia is administered using butorphenone (0.5–5.0 mg/kg s.c.). At day 14 after cuff placement, the animals are re-anesthetized with ether, the chest cavity opened, and then sacrificed by placement of a 22-gauge butterfly angiocatheter into the left ventricle and in situ constant pressure (100 mm Hg) perfusion with 0.9% saline for 1 min. followed by fixation with 4% paraformaldehyde in 0.1 M phosphate buffer, pH 7.3, for 10 min. The right atrium may be opened laterally and functioned as the outflow tract. Both left and right femoral arteries are then harvested, embedded in paraffin, and cut into transverse sections for routine light microscopy and immunohistochemistry. The inhibition of cathepsin S and cathepsin K at the site of vascular injury by systemic administration of cystatin C or TGF-$\beta_1$ may then be examined. Cathepsin K activity, for example, may be examined by monitoring specific cathepsin K cleavage sites in native collagen using differential staining with monoclonal antibodies to the amino-terminal and distal helical regions of collagen (Johnatty et al., 158 J. Immunol. 2327–333 (1997)).

Alternatively, acute vascular injury may be induced by carotid artery dilitation and endothethial cell denudation. Briefly, mice (C57/b16, 8 weeks old weighing approximately 25 g) are anesthetized on day 0 by i.p. injection of ketamine (80 mg/kg) and xylazine (5 mg/kg). The skin overlying the right carotid artery is prepared for surgery and surgery performed using sterile techniques. The biological response to vascular injury may be investigated using an airdrying model The animals are put on a standard diet and water ad libitium after surgery and post-operative analgesia is administered using butorphenol (0.5–5.0 mg/kg). At day 3, 7, or 28 the animals are re-anesthetized with ketamine and xylazine, the chest cavity opened, and the animal sacrificed by placement of a 22-gauge butterfly angiocatheter into the left ventricle for in situ constant pressure (100 mg) perfusion with 0.9% saline for 1 minute followed by fixation with 4% formaldehyde in 0.1M phosphate buffer, pH 7.3, for ten minutes. The right atrium may be opened laterally and functioned as the outflow tract. Both left and right carotid arteries are harvested, and embedded in paraffin for examination as discussed above in EXAMPLE 1.

Briefly, i.p. injections of cystatin C may be carried out every 48 hours. Spleen cells may be isolated and labeled with [$^{125}$I]-Z-Tyr-Ala-CHN$_2$, a cysteine protease active site probe, as previously described, and inhibition of cathepsins S and K monitored. Both cystatin C and TGF-$\beta_1$ compositions may be prepared as described above.

The foregoing description has been presented only for the purposes of illustration and is not intended to limit the invention to the precise form disclosed, but by the claims appended hereto.

We claim:

1. A method of treating atherosclerosis in a subject, comprising identifying a subject suffering from atherosclerosis and administering to said subject a composition comprising cystatin C in an effective amount to reduce a symptom of atherosclerosis.

2. The method of claim 1, wherein said composition is administered directly to an atherosclerotic plaque.

3. The method of claim 1, wherein said composition is administered systemically.

4. A method of reducing the risk of developing atherosclerosis in a subject, comprising identifying a subject at risk of developing atherosclerosis and administering to said subject a composition comprising cystatin C in an effective amount to reduce the risk of developing atherosclerosis.

5. The method of claim 4, wherein said subject is at risk of developing atherosclerosis.

* * * * *